United States Patent
McLaughlin

(10) Patent No.: US 10,493,393 B2
(45) Date of Patent: Dec. 3, 2019

(54) FRAGRANCE FILTER ASSEMBLY

(71) Applicant: Willie McLaughlin, New Orleans, LA (US)

(72) Inventor: Willie McLaughlin, New Orleans, LA (US)

( * ) Notice: Subject to any disclaimer, the term of this patent is extended or adjusted under 35 U.S.C. 154(b) by 178 days.

(21) Appl. No.: 15/678,269

(22) Filed: Aug. 16, 2017

(65) Prior Publication Data

US 2019/0054408 A1     Feb. 21, 2019

(51) Int. Cl.
| | | |
|---|---|---|
| *B01D 46/00* | (2006.01) | |
| *B01D 50/00* | (2006.01) | |
| *B01D 46/52* | (2006.01) | |
| *F24F 3/16* | (2006.01) | |
| *B60H 3/00* | (2006.01) | |
| *B01D 46/10* | (2006.01) | |
| *B60H 3/06* | (2006.01) | |

(52) U.S. Cl.
CPC ..... *B01D 46/0038* (2013.01); *B01D 46/0005* (2013.01); *B01D 46/10* (2013.01); *B01D 46/521* (2013.01); *B01D 46/523* (2013.01); *B01D 50/00* (2013.01); *B60H 3/0007* (2013.01); *B60H 3/0014* (2013.01); *F24F 3/1603* (2013.01); *A61L 2209/16* (2013.01); *B01D 2279/35* (2013.01); *B01D 2279/50* (2013.01); *B60H 3/0608* (2013.01); *F24F 2003/1689* (2013.01)

(58) Field of Classification Search
CPC ..... B01D 46/0038; B01D 46/10; B01D 50/00
USPC .............................................. 55/501; 96/222
See application file for complete search history.

(56) References Cited

U.S. PATENT DOCUMENTS

| | | |
|---|---|---|
| 4,604,114 A | 8/1986 | Ward |
| 4,875,912 A | 10/1989 | Fulmer |
| 5,258,051 A | 11/1993 | Anderson |
| D344,327 S | 2/1994 | Tavasso |
| 5,415,675 A | 5/1995 | Powers et al. |
| 5,817,168 A | 10/1998 | Wheless |
| 5,820,791 A | 10/1998 | Canale |
| 2006/0272304 A1* | 12/2006 | Louis Schupp ........... A61L 9/04 55/501 |

FOREIGN PATENT DOCUMENTS

WO     WO2014006458     1/2014

* cited by examiner

*Primary Examiner* — Robert A Hopkins

(57) ABSTRACT

A fragrance filter assembly for releasing a fragrance into an HVAC system includes a filter unit that may positioned in an intake of an HVAC system. The filter unit inhibits particles from passing through the intake. A plurality of strips each of the strips is coupled to the filter unit. Each of the strips is infused with a fragrance wherein each of the strips is configured to release the fragrance into the intake when the HVAC system is turned on thereby enhancing a smell of air urged by the HVAC system.

6 Claims, 2 Drawing Sheets

FRAGRANCE FILTER ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to filter devices and more particularly pertains to a new filter device for releasing a fragrance into an HVAC system.

BRIEF SUMMARY OF THE INVENTION

An embodiment of the disclosure meets the needs presented above by generally comprising a filter unit that may positioned in an intake of an HVAC system. The filter unit inhibits particles from passing through the intake. A plurality of strips each of the strips is coupled to the filter unit. each of the strips is infused with a fragrance wherein each of the strips is configured to release the fragrance into the intake when the HVAC system is turned on thereby enhancing a smell of air urged by the HVAC system.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
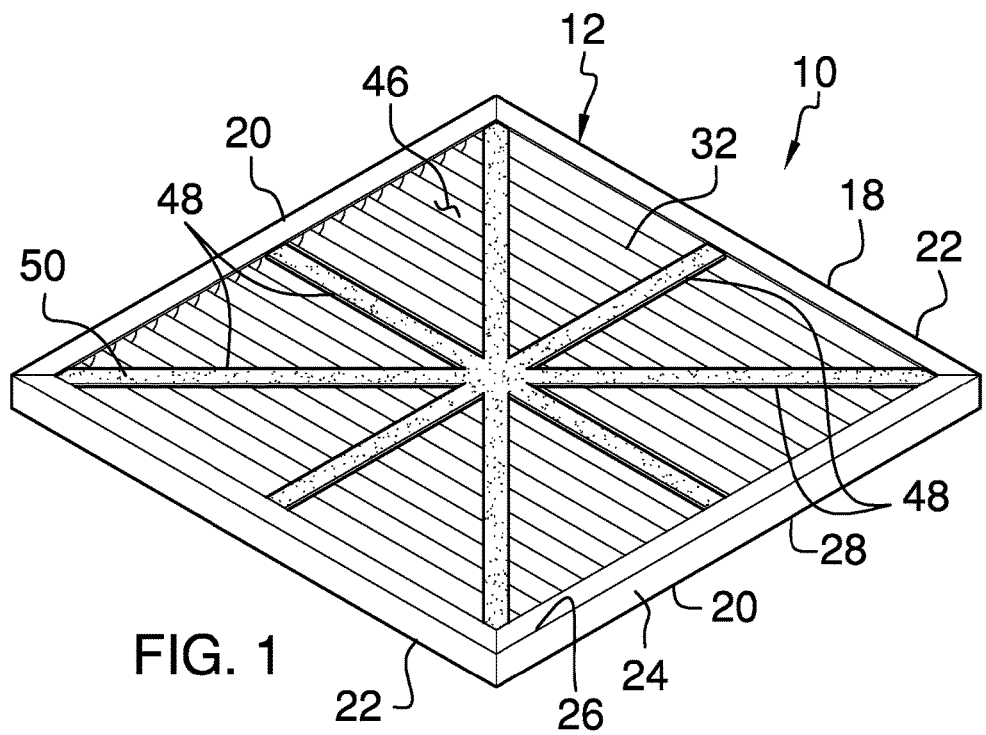
FIG. 1 is a perspective view of a fragrance filter assembly according to an embodiment of the disclosure.
Figure 2:
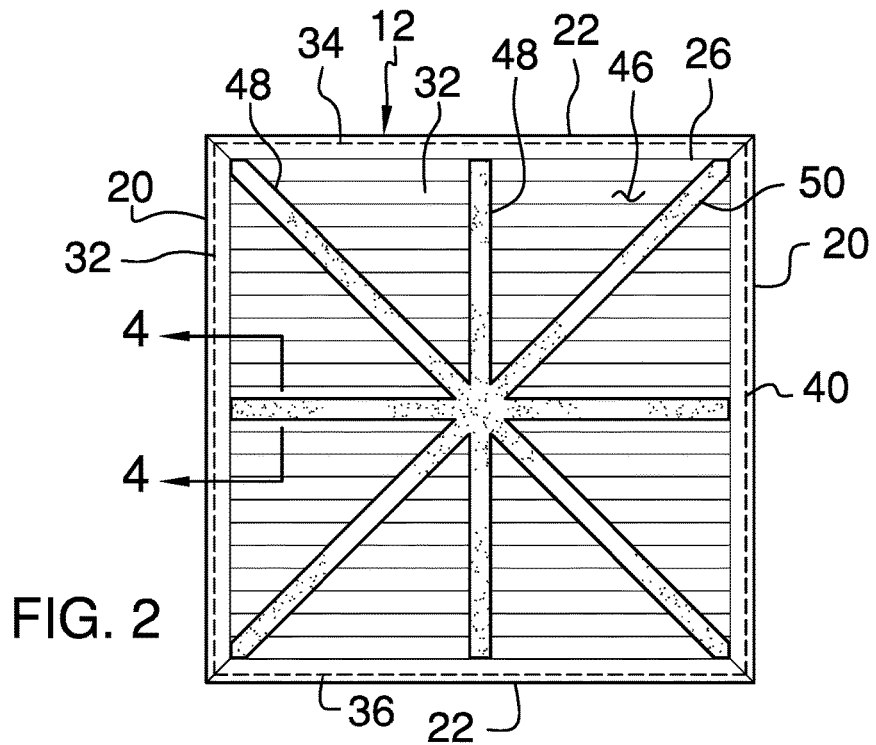
FIG. 2 is a back view of an embodiment of the disclosure.
Figure 3:
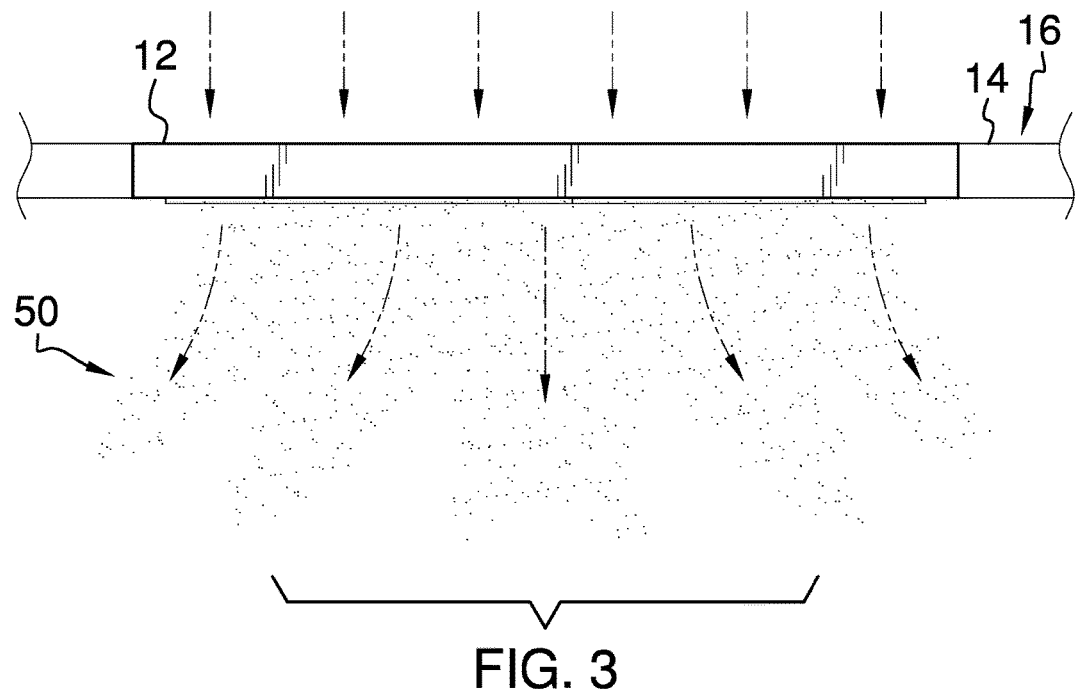
FIG. 3 is a perspective in-use view of an embodiment of the disclosure.
Figure 4:
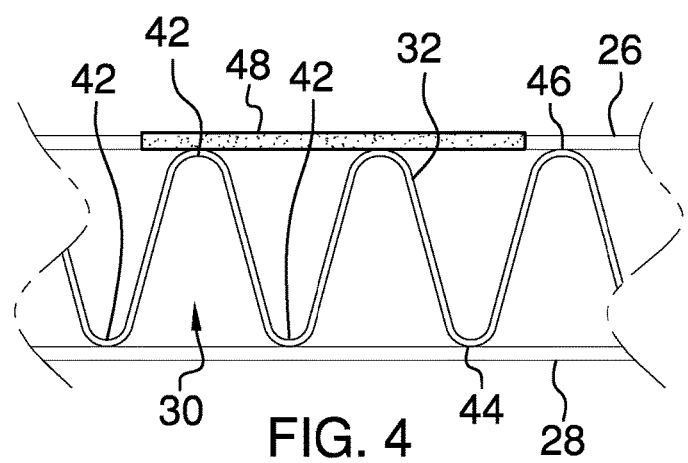
FIG. 4 is a cross sectional view taken along line 4-4 of FIG. 2 of an embodiment of the disclosure.

With reference now to the drawings, and in particular to FIGS. 1 through 4 thereof, a new filter device embodying the principles and concepts of an embodiment of the disclosure and generally designated by the reference numeral 10 will be described.

As best illustrated in FIGS. 1 through 4, the fragrance filter assembly 10 generally comprises a filter unit 12 that is positioned in an intake 14 of an HVAC system 16. In this way the filter unit 12 inhibits particles from passing through the intake 14. The HVAC system 16 may be a residential forced air system or the like. The filter unit 12 comprises a frame 18 that has a pair of longitudinal members 20 each extending between a pair of lateral members 22. The longitudinal members 20 are spaced apart from each other such that the frame 18 has rectangular shape. Each of the longitudinal 20 and lateral 22 members has a first portion 24 extending between a second portion 26 and a third portion 28. The second portion 26 and the third portion 28 are spaced apart to define a space 30 between the second portion 26 and the third portion 28 corresponding to each of the longitudinal 20 and lateral 22 members.

The filter unit 12 includes a filter 32 that has a front edge 34, a back edge 36, a first lateral edge 38 and a second lateral edge 40. The filter 32 has a plurality of pleats 42. Each of the pleats 42 extends between the first lateral edge 38 and the second lateral edge 40. The pleats 42 are spaced apart from each other and are distributed between the front edge 34 and the back edge 36.

Each of the front edge 34 and the back edge 36 is positioned in the space 30 corresponding to an associated one of the lateral members 22. Each of the first lateral edge 38 and the second lateral edge 40 is positioned in the space 30 corresponding to an associated one of the longitudinal members 20. The filter 32 is comprised of a fluid permeable material, such as micro fiber or the like, to pass air therethrough while capturing particles. Additionally, the filter 32 has a first surface 44 and a second surface 46. The filter unit 12 is positioned in the intake 14 such that air passes through the filter 32 from the first surface 44 to the second surface 46.

A plurality of strips 48 is provided and each of the strips 48 is coupled to the filter unit 12 and each of the strips 48 is infused with a fragrance 50. Thus, each of the strips 48 releases the fragrance 50 into the intake 14 when the HVAC system 16 is turned on. In this way the fragrance 50 enhances a smell of air urged by the HVAC system 16. Each of the strips 48 is coupled to and extends across the frame 18 has the plurality of strips 48 lying on the filter 32. Each of the strips 48 intersects each other at a center of the filter 32. Moreover, each of the strips 48 is positioned on the second surface 46 of the filter 32. In this way the filter 32 inhibits particles from collecting on the strips 48 when the HVAC unit urges air through the filter 32.

In use, the filter unit 12 is positioned in the intake 14 of the HVAC unit to filter 32 air that is urged into the intake 14. The fragrance 50 in the strips 48 is released into the air when the HVAC unit urges air through the intake 14. Additionally, the filter unit 12 is positioned in the intake 14 such that the air passes through the first surface 44 to the second surface 46 of the filter 32. In this way the filter 32 inhibits the strips 48 from being covered by particles thereby potentially inhibiting the fragrance 50 from being released into the HVAC unit. The filter unit 12 is replaced when the first surface 44 of the filter 32 becomes covered with particles.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A fragrance filter assembly being configured to release a fragrance into an HVAC system, said assembly comprising:
   a filter unit being configured to be positioned in an intake of an HVAC system thereby facilitating said filter unit to inhibit particles from passing through the intake, said filter including a frame; and
   a plurality of strips each of said strips being coupled to said filter unit, each of said strips being infused with a fragrance wherein each of said strips is configured to release the fragrance into the intake when the HVAC system is turned on thereby enhancing a smell of air urged by the HVAC system each of said strips being coupled to and extending across said frame having said plurality of strips lying on said filter, each of said strips intersecting each other at a center of said filter such that said strips are radially arranged extending continuously and linearly from said center of said filter to said frame.

2. The assembly according to claim 1, wherein said frame has a pair of longitudinal members each extending between a pair of lateral members, said longitudinal members being spaced apart from each other such that said frame has rectangular shape.

3. The assembly according to claim 2, wherein each of said longitudinal and lateral members has a first portion extending between a second portion and a third portion to define a space between said second portion and said third portion corresponding to each of said longitudinal and lateral members.

4. The assembly according to claim 1, further comprising a filter having a front edge, a back edge, a first lateral edge and a second lateral edge, said filter having a plurality of pleats, each of said pleats extending between said first lateral edge and said second lateral edge, said pleats being spaced apart from each other and being distributed between said front edge and said back edge.

5. The assembly according to claim 4, wherein:
   said frame has a pair of longitudinal members and a pair of lateral members, each of said longitudinal and lateral members having a space therein; and
   each of said front edge and said back edge being positioned in said space corresponding to an associated one of said lateral members, each of said first lateral edge and said second lateral edge being positioned in said space corresponding to an associated one of said longitudinal members, said filter being comprised of a fluid permeable material wherein said filter is configured to pass air therethrough while capturing particles.

6. A fragrance filter assembly being configured to release a fragrance into an HVAC system, said assembly comprising:
   a filter unit being configured to be positioned in an intake of an HVAC system thereby facilitating said filter unit to inhibit particles from passing through the intake, said filter unit comprising:
      a frame having a pair of longitudinal members each extending between a pair of lateral members, said longitudinal members being spaced apart from each other such that said frame has rectangular shape, each of said longitudinal and lateral members having a first portion extending between a second portion and a third portion to define a space between said second portion and said third portion corresponding to each of said longitudinal and lateral members, and
      a filter having a front edge, a back edge, a first lateral edge and a second lateral edge, said filter having a plurality of pleats, each of said pleats extending between said first lateral edge and said second lateral edge, said pleats being spaced apart from each other and being distributed between said front edge and said back edge, each of said front edge and said back edge being positioned in said space corresponding to an associated one of said lateral members, each of said first lateral edge and said second lateral edge being positioned in said space corresponding to an associated one of said longitudinal members, said filter being comprised of a fluid permeable material wherein said filter is configured to pass air therethrough while capturing particles; and
   a plurality of strips each of said strips being coupled to said filter unit, each of said strips being infused with a fragrance wherein each of said strips is configured to release the fragrance into the intake when the HVAC system is turned on thereby enhancing a smell of air urged by the HVAC system, each of said strips being coupled to and extending across said frame having said plurality of strips lying on said filter, each of said strips intersecting each other at a center of said filter such that said strips are radially arranged extending continuously and linearly from said center of said filter to said frame.

* * * * *